US005693261A

United States Patent [19]
Krzystowczyk et al.

[11] Patent Number: 5,693,261
[45] Date of Patent: Dec. 2, 1997

[54] PREPARATION OF PENTAFLUOROPHENYL COMPOUNDS

[75] Inventors: Niomi L. Krzystowczyk; Steven P. Diefenbach, both of Baton Rouge; Wendy L. Lemoine, Greenwell Springs, all of La.

[73] Assignee: Albemarle Corporation, Richmond, Va.

[21] Appl. No.: 513,065

[22] Filed: Aug. 9, 1995

Related U.S. Application Data

[63] Continuation of Ser. No. 392,001, Feb. 21, 1995, abandoned.

[51] Int. Cl.$^6$ .................... C07F 7/08; C07F 3/02
[52] U.S. Cl. ............ 260/665 G; 556/489; 556/43; 556/52; 556/58; 556/112; 556/140; 556/136; 556/121; 556/187; 556/170; 568/1; 570/127
[58] Field of Search ............ 260/665 G; 556/489, 556/43, 52, 58, 112, 140, 136, 121, 187, 170; 568/1; 570/127

[56] References Cited

U.S. PATENT DOCUMENTS

| | | | |
|---|---|---|---|
| 2,853,525 | 9/1958 | Wittig et al. | 260/606.5 |
| 2,880,242 | 3/1959 | Hennion | 260/606.5 |
| 2,880,243 | 3/1959 | Hennion | 260/606.5 |
| 2,939,885 | 6/1960 | Perrine, Jr. | 260/606.5 |
| 3,100,181 | 8/1963 | Ryznar et al. | 204/59 |
| 3,397,241 | 8/1968 | Smai et al. | 260/606.5 |
| 3,405,179 | 10/1968 | Wowk | 260/606.5 |
| 3,475,496 | 10/1969 | Smai et al. | 260/605.6 |
| 5,045,244 | 9/1991 | Marlett | 260/665 G |
| 5,242,625 | 9/1993 | Jones et al. | 260/665 G |
| 5,362,423 | 11/1994 | Ikeda et al. | 260/665 R |
| 5,387,727 | 2/1995 | Ikeda et al. | 570/143 |
| 5,399,780 | 3/1995 | Ikeda et al. | 568/1 |

FOREIGN PATENT DOCUMENTS

| | | | |
|---|---|---|---|
| 0520732 | 12/1992 | European Pat. Off. | C08F 10/00 |
| 0604959 | 7/1994 | European Pat. Off. | C07F 3/02 |
| 0604961 | 7/1994 | European Pat. Off. | C07F 5/02 |
| 0604963 | 7/1994 | European Pat. Off. | C07F 5/02 |

OTHER PUBLICATIONS

Massey, A.G. et al., J. Organometal. Chem., 2, (1964) 245–250.
Pohlmann, J.L. et al., Z. Naturfurschg. 20b, 5–11 (1965).
Harper, R.J., Jr. et al., J. Org. Chem., 29, (1964) 2385–2389.
Respers et al., J. Organometal. Chem., 11 (1968) 619–622.
CA 139179s, vol. 100, No. 17, (1984).
Tamborski, Christ, et al, "Synthesis of Polyfluoroaromatic Magnesium Compounds Through the Exchange Reaction", J. Organometal. Chem., 26 (1971) 153–156, Jun. 1971.

Primary Examiner—Paul F. Shaver
Attorney, Agent, or Firm—Philip M. Pippenger

[57] ABSTRACT

Pentafluorophenylmagnesium halides are prepared by a Grignard exchange reaction of hydrocarbylmagnesium halide with pentafluorochlorobenzene. The pentafluorophenylmagnesium halides are converted to pentafluorophenyl metal or metalloid derivatives by reacting them with metal or metalloid halides such as $BF_3$.

15 Claims, No Drawings

PREPARATION OF PENTAFLUOROPHENYL COMPOUNDS

This application is a continuation of application Ser. No. 08/392,001, filed Feb. 21, 1995, now abandoned.

This invention relates generally to the preparation of pentafluorophenyl derivatives and more specifically to the preparation of pentafluorophenylmagnesium compounds from chloropentafluorobenzene and the use of such magnesium compounds in the preparation of further pentafluorophenyl derivatives such as tris(pentafluorophenyl)borane and tetrakis(pentafluorophenyl)borates.

Pentafluorophenyl compounds such as tris(pentafluorophenyl)borane and tetrakis(pentafluorophenyl) borates are useful in forming olefin polymerization catalyst complexes with metallocenes. It is known to prepare these compounds by reacting pentafluorophenylmagnesium derivatives with boron halides. The pentafluorophenylmagnesium intermediates have been prepared by reacting pentafluorobromobenzene with an alkylmagnesium halide by an exchange reaction. Pentafluorobromobenzene is expensive to prepare. Pentafluorochlorobenzene is available at lower cost but, due to the generally known poor reactivity of chlorides versus bromides in exchange reactions it would not be expected to be a useful raw material for forming pentafluorophenylmagnesium halides. Surprisingly, we have found that pentafluorophenylmagnesium halides can be prepared in high conversions of 95–99% by a direct exchange between pentafluorochlorobenzene and alkylmagnesium compounds.

In accordance with this invention there is provided a process for preparing a pentafluorophenyl compound having the general formula $C_6F_5MgX$, wherein X is halogen, said process comprising reacting pentafluorochlorobenzene with a hydrocarbyl magnesium halide under conditions to form $C_6F_5MgX$.

Also provided is a process for preparing a pentafluorophenyl compound having the general formula $(C_6F_5)_nY$, where Y is a transition or main group element of Groups 4 to 14 of the Periodic Table other than carbon and n equals the valence of Y, said process comprising the steps of, (a) reacting pentafluorochlorobenzene with a hydrocarbyl magnesium halide under conditions so as to form a pentafluorophenylmagnesium halide, (b) reacting said pentafluorophenylmagnesium halide with a halide of Y, in a mole ratio of from about (0.8 to 1.2)n to 1, in an ether solvent under conditions so as to form a solution of an ether complex of said pentafluorophenyl compound, and (c) optionally recovering said pentafluorophenyl compound from said complex by solvent exchange. Also provided is a process for preparing a pentafluorophenyl compound having the general formula $(C_6F_5)_{n+1}YMgX$, where Y is a transition or main group element of Group 4 to 14 of the Periodic Table other than carbon and n is the valence of Y, said process comprising the steps of (a) reacting pentafluorochlorobenzene with a hydrocarbylmagnesium halide under conditions so as to form a pentafluorophenylmagnesium halide, and (b) reacting said pentafluorophenylmagnesium halide with a halide of Y, in a mole ratio of at least about 1.25 n to 1, under conditions so as to form $(C_6F_5)_{n+1}YMgX$.

To prepare the pentafluorophenylmagnesium halide, pentafluorochlorobenzene is reacted with a hydrocarbylmagnesium halide represented by the general formula RMgX where X is halogen, and preferably bromine or iodine and R is a $C_1$ to $C_{20}$, and preferably a $C_2$ to $C_{10}$, hydrocarbyl group such as, for example ethyl, propyl, propenyl, butyl, pentyl, hexyl, heptyl, octyl, nonyl, decyl, including their branched chain isomers such as, for example, isopropyl, isopropenyl, sec-butyl, tert-butyl, isobutyl, isopentyl, and cyclic alkyls such as for example, cyclohexyl and the like. Most preferred is isopropyl.

The amounts of reactants used can vary from stoichiometric amounts. Preferably, the pentafluorochlorobenzene to hydrocarbylmagnesium halide mole ratios range from about 1:1 to 10:1 and most preferably from about 1:1 to 2:1 in order to maximize the conversion of the hydrocarbylmagnesium halide and minimize side reactions such as the substitution of an alkyl group on the phenyl ring.

The reaction is carried out in an ether solvent. Non-limiting examples of suitable ethers include diethyl ether, dipropyl ether, diisopropyl ether, dibutyl ether, ethylene glycol, dimethyl ether, 2-methoxyethyl ether, tetrahydrofuran and the like. Preferred is diethyl ether.

The reaction can be carried out in a batch process or by slowly feeding one reagent into the other at a temperature of from about −40° to 100° C. and then the mixture is reacted at temperature of from about 20° to 250° C. The reaction can be run at atmospheric pressure but, preferably is carried out in a sealed reactor to avoid loss of solvent, in which case the release of solvent vapors and gaseous by-products into the sealed reactor will cause the pressure to increase. Reaction times of from about 0.5 to 50 hours are used to complete the reaction.

The pentafluorophenyl derivatives which are prepared in accordance with the process of the invention can be represented by the general formulas $(C_6F_5)_nY$ (I) and $(C_6F_5)_{n+1}YMgX$ (II) where n is the valence of Y, X is halogen and Y is a transition or main group element of Groups 4 to 14 of the Periodic Table according to the new IUPAC notation. Non-limiting examples of the elements include titanium, zirconium, hafnium, vanadium, chromium, magnesium, iron, ruthenium, zinc, copper, aluminum, boron, silicon and the like. Halides of these elements ($YX_n$) such as aluminum chloride and boron trifluoride, and the like are reacted with the pentafluorophenylmagnesium halides in molar proportions to selectively produce primarily compounds of either formula I, $(C_6F_5)_nY$, or formula II, $(C_6F_5)_{n+1}YMgX$. The non-selected compound is usually produced in at least small amounts as a by-product. Compounds of formula (I) are preferentially produced by selecting mole ratios of pentafluorophenylmagnesium halide to $YX_n$ compound of from about (0.8 to 1.2)n to 1 and compounds of formula II are preferentially produced by selecting mole ratios of at least about 1.25 n to 1 and preferably from about (1.25 to 1.5)n to 1.

The reaction is carried out in an ether solvent and the same ethers used in the reaction to form the pentafluorophenylmagnesium halide are suitable. In fact, the halide reactant can be conveniently added to the pentafluorophenylmagnesium halide reaction mixture, preferably as its ether complex, at temperatures of from about −40° to 200° C. and then the reaction is completed at temperatures of from about 20° to 250° C. for times ranging from 0.5 to 50 hours at elevated temperatures to several weeks at ambient temperature.

The products can be recovered by solvent exchange techniques. For example a hydrocarbon solvent which has a higher boiling point is added to the reaction mixture and the ether is removed by azeotropic distillation leaving a hydrocarbon solution of the formula I product and a precipitate of the magnesium halide salt and the formula II co-product. As discussed above, the relative proportion of each product obtained will depend upon the mole ratio of reactants. The solution of the formula I product is then separated from the precipitate and the formula II co-product can be separated from the inorganic magnesium salts by solvent extraction, such as with diethyl ether. The heavy precipitate may damage the agitators during the solvent exchange step. Therefore, a precipitating agent can be added to the reaction mixture, which effectively breaks up the ether complex of the product and salts and thereby precipitates the majority of the salts, such that 80 to 90% of the salts can be removed such as by filtration, prior to the solvent exchange step while leaving the product in solution. Preferred precipitating agents are ethers having from about 4 to 20 carbons. Non-limiting examples of suitable ethers include alkyl and aryl mono-ethers such as diisopropyl ether, di-n-butyl ether, methyl tert-butyl ether, diphenyl ether, diethers such as dimethoxyethane, and cyclic ethers such as 1,4-dioxane, 1,3-dioxolane, 2-methyl-1,3-dioxolane, N-methylmorpholine, and triethers such as 1,3,5-trioxane and the like. Tetrahydrofuran is not effective to precipitate the salts. The precipitating agent is added in amounts of from about 0.1 to 1 mole per mole of magnesium such that none of the precipitating agent becomes complexed with the formula I product.

Alternatively, an ether like 1,4-dioxane can be added to the halide reactant such as $BF_3$.etherate in diethylether solution. This solution is then added to the diethyl ether solution of pentafluorophenylmagnesium halide in the usual manner. This would lead to the formation of $(C_6F_5)_3B$ etherate and the magnesium halide salts would precipitate as the dioxane complex as they are formed.

Suitable hydrocarbon solvents for the solvent exchange are selected such that a solvent is used that boils above the boiling point of the ether solvent such that the ether is removed as an azeotrope to leave a solution of the formula I product in the hydrocarbon solvent and a precipitate of the remaining magnesium salts and the formula II product. The latter product can be separated from the salts by an ether extraction after separating the precipitate from the product solution such as by filtration of the hot hydrocarbon solvent solution. Non-limiting examples of suitable hydrocarbon solvents having boiling points of from about 65° to 200° C. include hexane, heptane, Isopar E, octane, nonane, decane, hexadecane, benzene, toluene, xylenes, and the like, including mixtures. The hydrocarbon solvent is used in proportions of from about 50 to 99 percent by volume of the total volume of product solution.

The invention is further illustrated by, but is not intended to be limited to, the following examples.

EXAMPLE 1

In a drybox, 31.45 g of chloropentafluorobenzene ($C_6F_5Cl$) (0.155 moles) and 64.42 g of a 2 molar ether solution of isopropylmagnesium bromide (iPrMgBr) (0.141 moles) were charged to a Fisher Porter reactor and heated to 60° C. for 4.5 hours. The sample showed a 99.06% conversion to pentafluorophenylmagnesium bromide ($C_6F_5MgBr$) by NMR. Repeating the preparation, but using mole ratios of $C_6F_5Cl$ to iPrMgBr of about 1.55 to 1 and 2 to 1, gave conversions of iPrMgBr to $C_6F_5MgBr$ of 98% and 93 to 95%, respectively.

EXAMPLE 2

131 mmols of the $C_6F_5MgBr$ solution above was charged to a 4 neck roundbottom flask. 5.84 g (41.4 mmols) of $BF_3$:etherate was charged to the solution at 0° C. The solution was then allowed to warm to room temperature and stirred overnight. The reaction showed an 81% yield of $(C_6F_5)_3B$ in ether.

EXAMPLE 3

40 mmoles of $C_6F_5MgBr$ solution in ether was reacted with 10 mmols of $BF_3$:etherate at room temperature. The reaction was allowed to stir and the final conversion found to be 79% with about 63.1% of the product as $(C_6F_5)_4BMgBr$ and 43.6% of the product as $(C_6F_5)_3B$. The reaction time was 3 weeks (could be reduced if the reaction mixture was warmed).

What is claimed is:

1. A process for preparing a pentafluorophenyl compound having the general formula $C_6F_5MgX$, wherein X is halogen, said process comprising reacting pentafluorochlorobenzene with a $C_3$ to $C_{20}$ hydrocarbylmagnesium halide under conditions to form $C_6F_5MgX$.

2. The process according to claim 1 wherein the reaction is carried out in an ether solvent.

3. The process according to claim 1 wherein the mole ratio of pentafluorochlorobenzene to hydrocarbylmagnesium halide ranges from about 1:1 to 10:1.

4. The process according to claim 1 wherein the hydrocarbylmagnesium halide is a propylmagnesium halide.

5. The process according to claim 1 wherein pentafluorochlorobenzene is reacted with isopropylmagnesium bromide in a mole ratio ranging from about 1:1 to 2:1 in an ether solvent to provide pentafluorophenylmagnesium bromide.

6. A process for preparing a pentafluorophenyl compound having the general formula $(C_6F_5)_nY$, where Y is a transition or main group element of Groups 4 to 14 of the Periodic Table other than carbon and n equals the valence of Y, said process comprising the steps of, (a) reacting pentafluorochlorobenzene with a hydrocarbyl magnesium halide under conditions so as to form a pentafluorophenylmagnesium halide, (b) reacting said pentafluorophenylmagnesium halide with a halide of Y, in a mole ratio of from about (0.8 to 1.2)n to 1, in an ether solvent under conditions so as to form a solution of an ether complex of said pentafluorophenyl compound, and (c) optionally recovering said pentafluorophenyl compound from said complex by solvent exchange.

7. The process according to claim 6 wherein pentafluorophenylmagnesium halide is reacted with $BF_3$ and the pentafluorophenylcompound is $(C_6F_5)_3B$.

8. A process for preparing a pentafluorophenyl compound having the general formula $(C_6F_5)_{n+1}YMgX$, where Y is a transition or main group element of Group 4 to 14 of the Periodic Table other than carbon and n is the valence of Y, said process comprising the steps of (a) reacting pentafluorochlorobenzene with a hydrocarbylmagnesium halide under conditions so as to form a pentafluorophenylmagnesium halide, and (b) reacting said pentafluorophenylmagnesium halide with a halide of Y, in a mole ratio of at least about 1.25 n to 1, under conditions so as to form $(C_6F_5)_{n+1}YMgX$.

9. The process according to claim 8 wherein pentafluorophenylmagnesium bromide is reacted with $BF_3$ and the pentafluorophenyl compound is $(C_6F_5)_4BMgBr$.

10. The process according to claim 6 wherein said hydrocarbyl magnesium halide is a $C_3$ to $C_{20}$ hydrocarbyl magnesium halide.

11. The process according to claim 10 wherein said hydrocarbyl magnesium halide is a propylmagnesium halide.

12. The process according to claim 6 wherein the step (a) pentafluorochlorobenzene is reacted with isopropylmagnesium bromide in a mole ratio range from about 1:1 to 2:1 in a dialkyl ether solvent to provide pentafluorophenylmagnesium bromide.

13. The process according to claim 8 wherein said hydrocarbyl magnesium halide is a $C_3$ to $C_{20}$ hydrocarbyl magnesium halide.

14. The process according to claim 13 wherein said hydrocarbyl magnesium halide is a propylmagnesium halide.

15. The process according to claim 8 wherein the step (a) pentafluorochlorobenzene is reacted with isopropylmagnesium bromide in a mole ratio range from about 1:1 to 2:1 in a dialkyl ether solvent to provide pentafluorophenylmagnesium bromide.

* * * * *